US012657988B2

(12) United States Patent
Rojas et al.

(10) Patent No.: US 12,657,988 B2
(45) Date of Patent: Jun. 16, 2026

(54) BREAD VENDING MACHINE WITH ON-THE-SPOT TOASTING

(71) Applicant: GRUPO BIMBO, S.A.B. DE C.V., Mexico City (MX)

(72) Inventors: Carlos Rojas, Mexico City (MX); Robert Chernoff, Mexico City (MX); Benjamin Cosgrove, Mexico City (MX)

(73) Assignee: GRUPO BIMBO, S.A.B. DE C.V., Mexico City (MX)

( * ) Notice: Subject to any disclaimer, the term of this patent is extended or adjusted under 35 U.S.C. 154(b) by 692 days.

(21) Appl. No.: 17/983,620

(22) Filed: Nov. 9, 2022

(65) Prior Publication Data

US 2023/0351837 A1 Nov. 2, 2023

(30) Foreign Application Priority Data

Apr. 29, 2022 (MX) .................... MX/a/2022/005269

(51) Int. Cl.
*G07F 17/00* (2006.01)
*A61L 2/10* (2026.01)
*G07F 9/00* (2006.01)

(52) U.S. Cl.
CPC ............ *G07F 17/0078* (2013.01); *A61L 2/10* (2013.01); *G07F 9/009* (2020.05)

(58) Field of Classification Search
CPC .... A47J 37/08; A47J 37/0864; A47J 37/0964; G07F 17/0078; G07F 11/10; G07F 11/28; G07F 9/009; G07F 9/00
See application file for complete search history.

(56) References Cited

U.S. PATENT DOCUMENTS

| | | | | |
|---|---|---|---|---|
| 5,562,183 A | * | 10/1996 | Naramura | A21C 9/04 |
| | | | | 186/49 |
| 5,611,456 A | * | 3/1997 | Kasper | G07F 11/22 |
| | | | | 221/242 |
| 2009/0237421 A1 | * | 9/2009 | Kim | G06F 3/0485 |
| | | | | 345/173 |
| 2017/0165566 A1 | * | 6/2017 | Froy | G07F 17/3209 |
| 2017/0324794 A1 | * | 11/2017 | Jeong | H04L 67/025 |
| 2020/0357220 A1 | * | 11/2020 | Gauger | G07F 17/0078 |
| 2022/0172549 A1 | * | 6/2022 | Chung | G06Q 20/3278 |
| 2022/0236851 A1 | * | 7/2022 | Yamada | G06F 3/044 |

FOREIGN PATENT DOCUMENTS

WO WO-2018222168 A2 * 12/2018 ............. G07F 9/002

* cited by examiner

*Primary Examiner* — Timothy R Waggoner
(74) *Attorney, Agent, or Firm* — MaxGoLaw PLLC

(57) ABSTRACT

A vending machine is provided for vending pieces of bread that are toasted on the spot. The vending machine includes a control module; a toaster module; a screen displaying a graphical interface showing information related to the sale of the product; a contactless user interface for selecting the desired type and quantity of product; a storage device for storing the pieces of bread or product for sale; a pair of product feed modules set up to receive product from the storage device and feed a toaster module with the product selected by the user; an exit device allowing the exit of the product piece halves from underneath the toaster module, and a transport devices. The product halves are slid and conveyed to an exit outside the housing of the vending machine so that the user can take the purchased product.

15 Claims, 9 Drawing Sheets

BREAD VENDING MACHINE WITH ON-THE-SPOT TOASTING

FIELD OF APPLICATION OF THE INVENTION

The present invention relates to a vending machine for toasted bread pieces. Specifically, this is a toasted bread vending device comprising a novel toaster module that toasts up to two pieces of bread of different types, with each piece of bread consisting of two halves, when a user selects the type of bread of their choice via a contactless user interface with the device described in the present invention.

BACKGROUND TO THE INVENTION

There are a wide variety of food and beverage vending machines available today, however, most of these types of vending machines use a refrigeration system to keep the beverages and food cold for sale to a user. Other types of vending machines only sell hot beverages.

There are also self-service stations in commercial food establishments where the user selects the desired solid food from a refrigerator or display case, such as sandwiches, snacks, etc., and then heats it for consumption using a microwave oven in the self-service station.

However, using a self-service station presents the main drawback related to the hygiene of the food once it is ready for consumption. The food is handled by the user from selection, followed by payment via coins or banknotes and finally the manual operation of the microwave oven to heat the food. In addition, it should be considered that these devices are exposed to the public, meaning that they are used by various users and not sanitised on a constant basis, which leads to these devices becoming areas of germ accumulation.

In this regard, patent document MX 181938 B discloses a vending machine equipped with a restricted access self-service station comprising a microwave oven. The vending machine includes a cabinet equipped with a refrigerated compartment containing multiple product selections, a compressor associated with the refrigerated compartment and tactile devices for selecting food products and vending them to a user. The microwave oven is set up inside the cabinet and shares common access to a power supply with the compressor. An access door is provided in the cabinet between the user and the microwave to limit access to the microwave. The door opens when selling a selection of products for a predetermined period of time, allowing the user to insert the sold product into the oven. After activation of an oven cooking switch by the user, the access door closes and the microwave operates to heat the sold product; once the microwave oven operating time elapses the access door of the vending machine reopens so that the user has access again and can remove the selected hot product from inside the oven; once the user closes the access door of said machine, the machine may vend another product.

Likewise, vending machines are known to exist for hot food such as pizzas, brioches, toast, etc., which do not require forced intervention by the user to heat a selected product, such as the one disclosed in patent document U.S. Pat. No. 5,555,793 comprising: an initial station for storing pre-packaged products in a suitable cooling chamber; a second station for cutting the protective package of the container inside which the product to be processed is present, a collection station set up to receive the product from the second station, formed by a clamp which is counterbalanced by springs and in such a way as to keep the product firmly held inside; a device for rotating the clamp around one of its axes to arrange the clamp vertically with respect to the loading position of the clamp; a mobile cooking station capable of descending vertically for cooking and ascending once cooking is completed; a device for removing the processed product; a device for feeding a strip of napkins arranged along a perpendicular axis so that the product is wrapped in the napkins before it appears in the distribution slot for hygienic intake by the consumer; and electronic controllers suitable for interrupting the production cycle in the presence of abnormal conditions.

However, such hot food vending machines usually require constant preventive and corrective maintenance due to the diverse array of elements that constitute them; for example, napkin strip feeding device mechanisms often get stuck during the wrapping process of the final product due to the humidity present inside the machine, generated by the refrigeration or freezing station. Moreover, these machines consume a considerable amount of electrical energy because they must keep the products refrigerated or frozen, and the machine must also preheat the oven so that it reaches its ideal temperature once the product reaches the cooking station.

Furthermore, the vending machine of document U.S. Pat. No. 5,555,793 does not include any disinfection device for disinfecting the elements where the food is conveyed once its wrapping has been removed.

Another deficiency of this type of vending machine lies in the refrigeration or freezing station that is designed to contain food that has previously been packaged in hermetically sealed containers or wrappers, keeping the products at a constant preset refrigeration or freezing temperature. The refrigeration or freezing station thus consists of multiple metal containers where the products are stored and articulated devices to extract the product selected by the user, however the articulated devices are exposed to constant jams that can cause immobility in their mechanisms.

It is also important to consider that low temperatures and humidity inside such machines reduce the lifetime of mechanical and electrical components.

On the other hand, patent document U.S. Pat. No. 7,137, 529 B2 discloses a vending machine comprising a hermetically sealed refrigerated storage tank for containing and maintaining frozen or refrigerated pre-packaged foods; drive devices for moving said products within said reservoir; extraction devices for extracting a user-selected pre-packaged food from said storage container; control devices for controlling said drive device and said extraction device, characterised in that said drive devices, said extraction devices and said control devices are set up outside the cold storage tank; transport devices for transporting the pre-packaged food to a microwave oven for heating. The selected food, once it has been heated in the microwave oven, is thereby pushed out of the oven by a pushing device associated with the oven and is placed on a transfer device that guides the pre-heated food towards a distribution opening for delivery to the user. The vending machine thus keeps its mechanical and electrical components isolated from the humidity and temperatures generated by the cold storage tank.

However, such a vending machine also requires many sensors, actuators and mechanical components for its operation, which results in a considerable increase in its manufacturing cost, as well as in its preventive and corrective maintenance.

In addition, the state-of-the-art vending machines cited previously herein utilise touch interfaces for product selection by the user, as well as the use of coins or bills to make payment for the selected product. This has a disadvantage related to hygiene because these vending machines are installed in public spaces.

Another disadvantage presented by the state-of-the-art hot product vending machines is the waiting time for the machine to succeed in heating the selected product to a preset temperature, which can be tedious for the user. Therefore, a vending machine is required with a graphical interface that displays multimedia advertising to users during the waiting time before receiving the selected hot product.

Moreover, the state-of-the-art machines only sell and heat food products by using a microwave device or heat generating devices such as resistive elements, which must be preheated beforehand to avoid long waiting times during the heating of a product. As such, none of the state-of-the-art vending machines offer bread pieces for sale that are toasted at the time of purchase, achieving an appropriate toasted colour, temperature and consistency on their surfaces.

Consequently, there is a need for a vending machine that toasts bread pieces at the time of purchase with an efficient heating device that decreases the long waiting times required by conventional toasters, and that also provides the user or customer with the assurance of receiving warm, bacteria-free toast.

In addition, the vending machine detailed in the present invention has the ability to offer for sale to a user two toast type options to choose from, such as: English muffins or bagels.

The present invention thus possesses several features that make it completely different from existing vending machines, since it does not include conveying devices such as belts or mechanised grippers. As will be seen later in this description, the present invention has a special structural design that uses gravity to transport the product through the different modules and devices of the vending machine detailed in the present invention.

As will be described later, the toast vending machine includes devices for contactlessly ordering the purchase of at least one piece or two halves of toasted bread through manual gestures, wherein payment can be made by means of a card reader in communication with a bank payment system, or a coupon. Coupons can be activated for preset periods of time.

In another embodiment of the invention, a user, via a toast vending machine app installed on a user device, has the option of ordering at least one piece of toast from the machine once it recognise the user's identity via a facial recognition feature.

Those experienced in the art thus know the need for a product transport and delivery device such as the one proposed by the present invention, which is light for delivery vehicles, as well as safe and conducive to delivery persons in practice.

PURPOSES OF THE INVENTION

The main purpose of the present invention is to provide a bread piece vending machine that toasts bread halves at the time of purchase.

A second objective of the present invention is to provide a vending machine for toasted bread pieces that requires no user contact.

A third objective of the present invention is to provide a vending machine for toasted bread pieces that offers a choice of two types of bread pieces.

A fourth objective of the present invention is to provide a vending machine for toasted bread pieces that reduces the waiting time for toasting bread piece halves when compared to conventional toasting apparatuses.

A fifth objective of the present invention is to provide a toast piece vending machine with a contactless user interface that displays advertising of interest to the user during the waiting period.

A sixth objective of the present invention is to provide a vending machine for pieces of toasted bread with devices for disinfecting the medium in which the halves of a piece of bread are transported and delivered once toasted.

A seventh objective of the present invention is to provide a vending machine for pieces of toast in communication with a user mobile device wherein a user, via an app, chooses and orders at least one type piece of toast.

An eighth objective of the present invention is to provide a vending machine for pieces of toasted bread with devices allowing payment by means of a bank card (credit or debit) or a coupon code.

A ninth objective of the present invention is to provide a vending machine for pieces of toasted bread that offers its product with recognition capabilities allowing the machine to recognise the identity of a user.

SUMMARY OF THE INVENTION

The present invention relates to a vending machine for vending bread pieces (also named in the present description as "product") that are toasted on the spot, comprising: a housing containing the modules and components of the machine; a control module; a toaster module; a screen displaying a graphical interface showing information related to the sale of the product; an input interface consisting of multiple contactless input devices for selecting the desired type and quantity of product; storage devices for storing the halves of bread pieces or product for sale; a pair of product feed modules set up to receive product from the storage devices, and the ability to feed a toaster module with the product selected by the user (also named in the present disclosure as "the customer"); sliding devices that drive the halves of the selected product pieces towards the toaster module, which includes heat-generating devices that radiate heat onto the upper and lower surfaces of the selected product pieces for a period of time preset in the control module; an exit device allowing the product piece halves to exit from underneath the toaster module, and a transport device wherein the product halves are slid and driven towards an exit outside the vending machine housing described in the invention so that the user can take the selected product.

Specifically, the housing of the toast piece vending machine consists of a structural frame, a bottom wall, a right side wall, a left side wall, a back wall and a front wall consisting of: a pivoting upper front wall attached to the structural frame through pivoting elements or hinges and a lower front wall of smaller dimensions than the pivoting upper front wall. Through the pivoting upper front wall, one may access the inside of the housing for corrective or preventive maintenance of the machine when required.

The following detailed description presents the embodiments by way of illustration, including the best mode. While these embodiments are described in sufficient detail to enable those skilled in the art to implement the principles of the present disclosure, it will be understood that other embodiments may be implemented and that logical, mechanical and/or electrical changes may be made without departing from the spirit and scope of the principles of the present disclosure. Therefore, the detailed description herein is provided for illustrative and non-limiting purposes only.

In addition, for the sake of brevity, certain subcomponents of individual components, as well as other aspects of the system, may not be described in detail in this document. It should be noted that many alternative or additional functional relationships as well as physical couplings may be present in a practical system, for example, in a battery monitoring system. Such functional blocks can be implemented by any number of appropriate components configured to perform specific functions.

Certain terms are used throughout the following description and claims, to refer to particular features or components. As an expert in the field will appreciate, different people may refer to the same feature or component by different names. This document is intended to distinguish between components or features that differ in name, but not in function.

BRIEF DESCRIPTION OF THE DRAWINGS

Non-limiting and non-exhaustive implementations of the invention are described with reference to the following figures, wherein similar reference numerals refer to similar portions in all the various views, unless otherwise specified. Features and advantages of the disclosure of the present invention will become apparent from consideration of the attached description and drawings wherein.

DETAILED DESCRIPTION OF THE PREFERRED MODES

The applicant has developed, and herein discloses, a vending machine for toasted bread pieces. The toasted bread piece vending machine comprising a control module comprising a logic application arrangement such as a controller or a processor, a memory storing control logic related to the operation of the machine, and multimedia logic related to advertisements that are displayed to the customer during the waiting time it takes for the machine to toast and deliver the product. The control module is in communication with other devices and sensors of the modules that make up the machine as detailed below. A screen in communication with the control module displays a graphic interface for the sale of the product with the interaction of an input interface consisting of multiple non-contact sensors for selection by the user of the desired type and quantity of product pieces, by performing a hand movement on the corresponding sensor.

Storage device where the inventory of product for sale is stored; a pair of product feed modules arranged below the storage device where each feed module receives a pair of product pieces via force of gravity and pushes them towards a sliding device that moves the product piece halves towards the toasting chamber of the toaster module for toasting.

The control module activates up to its opposite end outside the vending machine detailed in the present invention.

Figure 1:
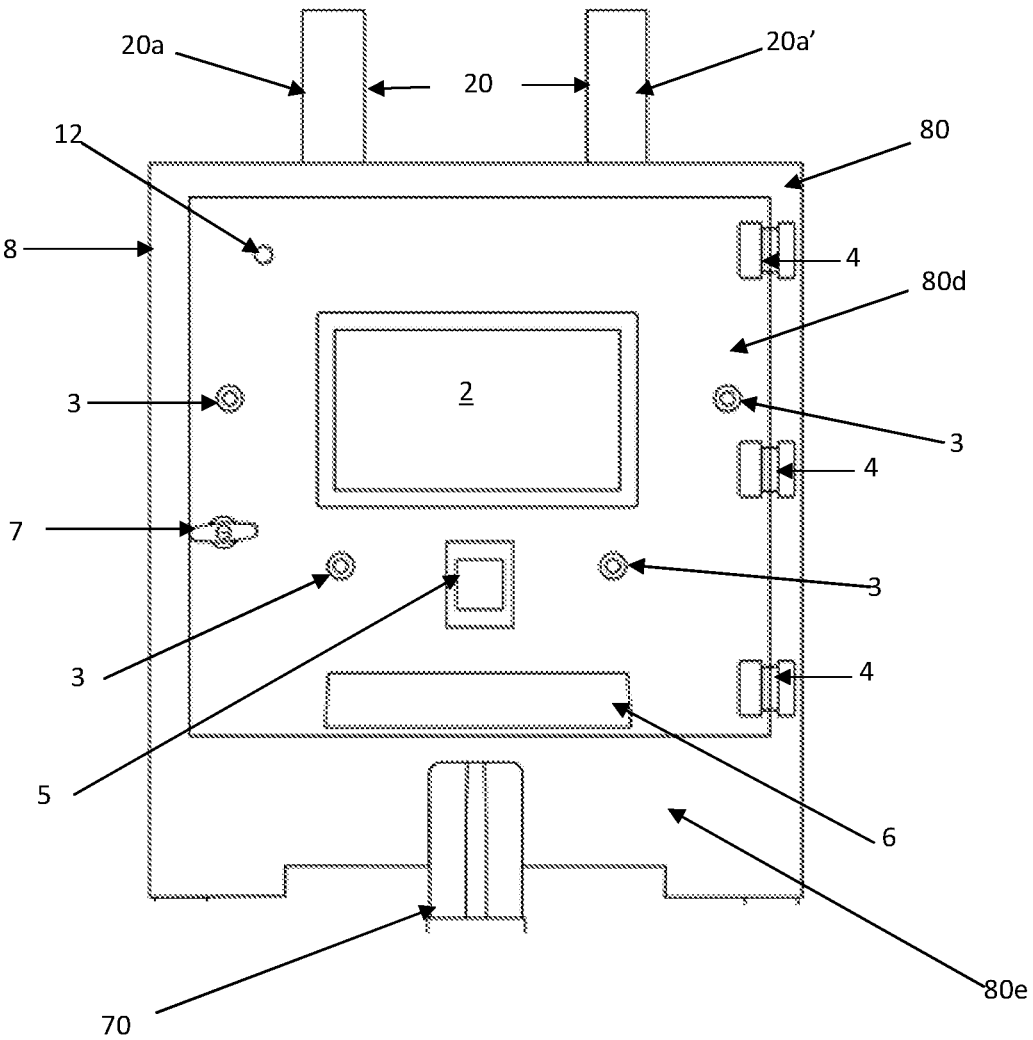
FIG. 1 shows a schematic front view of the toast piece vending machine detailed in the present invention.

FIG. 1 shows a front schematic view of a toast vending machine (1) comprising a housing (8) consisting of a structural frame (80), a right side wall, a left side wall, a rear wall (not shown), and a front wall consisting of: a pivoting upper front wall (80*d*) attached to the structural frame through pivoting elements or hinges (4) and a lower front wall (80*e*) of dimensions smaller than those of the pivoting upper front wall (80*e*).

The pivoting upper front wall (80*d*) comprises a cavity wherein the display (2) is attached, and four holes in which the four non-contact sensors that make up the input interface (3) of the vending machine (1) are mounted. Furthermore, a card reader (5) is attached to the surface of the pivoting upper front wall (80*d*) as a means of payment for the user to finalise the purchase of the desired product if the machine so requires. In another embodiment of the invention, the vending machine (1) is configured through the control logic of the control module (10) in such a way that it does not require a payment for the product requested by a user, replacing the payment by a recognition stage through its sensors; and once said condition is met, its operation is enabled to supply the required product. A PIR sensor (12) is also attached to the pivoting upper front wall (80*d*) as a safety device so that while the sensor (12) detects the presence of a person in front of the machine, the control module does not activate the operation of the UV lamp.

Continuing with FIG. 1, the lower front wall (80*e*) comprises a cavity into which the outlet end of the conveying medium (70) protrudes. A UV lamp (not shown) is mounted at the lower end of the pivoting upper front wall (80*d*) close to the lower front wall (80*f*) with a protective device (6). Said protective device (6) consists of a sheet with a reflecting bottom surface projecting towards the front of the machine (1) with a downward inclination of the same in such a way that light radiated by the UV lamp strikes the exit end of the transport device (70) and not the user.

A locking element (7) is available on the pivoting upper front wall (80*d*) as a security device for access to the internal part of the vending machine (1) detailed in the present invention and as an access device for performing preventive or corrective maintenance as required. Furthermore, in the upper part of the housing (70) there are protruding product storage devices (20) with a cylindrical shape consisting of a left front container (20*a*) and a left rear container (20*b*, not shown) wherein each left container (20*a* and 20*b*) stores one half of a piece of one type of product; and a right front container (20*a'*) and a right rear container (20*b'*, not shown)

wherein each right container (20a' and 20b') stores one half of one piece of a second type of product.

Figure 2:
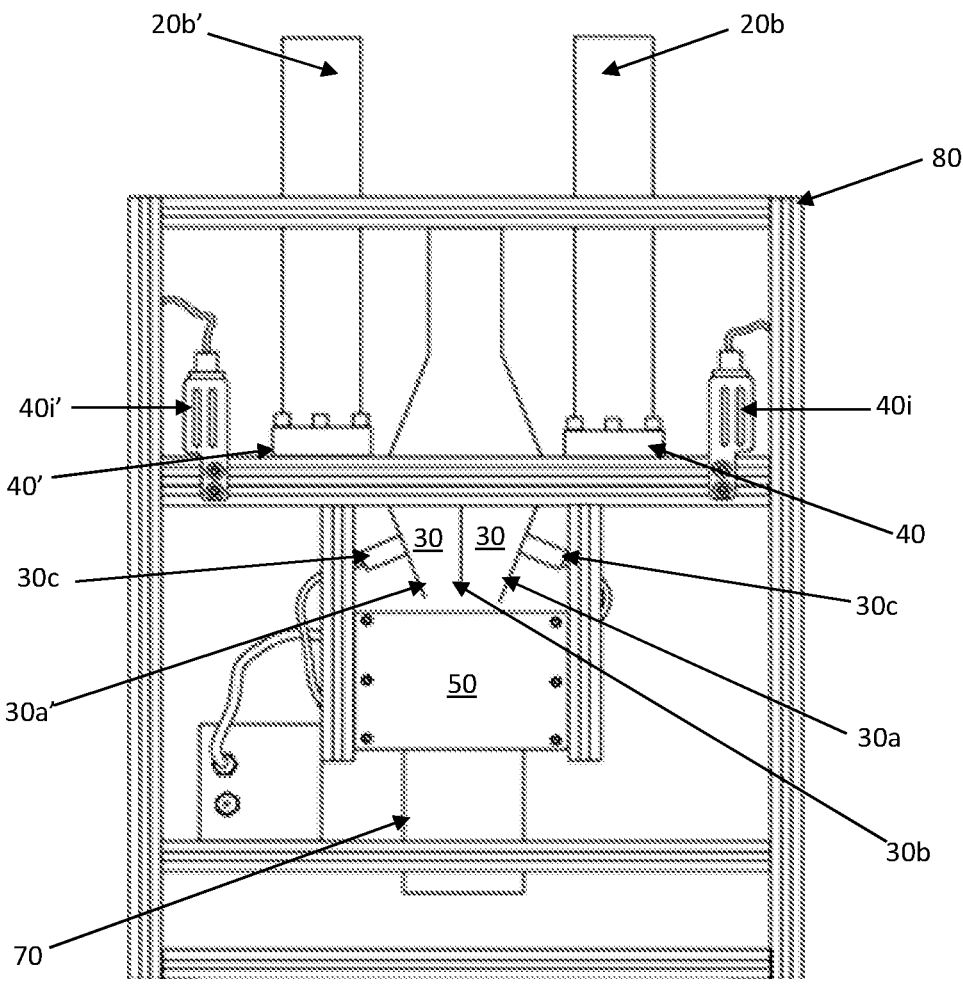
FIG. 2 shows a schematic rear view of the toast piece vending machine without the rear wall of its housing.

According to FIG. 2, which shows the rear of the vending machine detailed in the present invention (1) without the rear wall of the housing (8), the left containers (20a and 20b) are attached over a left feed module (40) while the right containers (20a' and 20b') are attached over a right feed module (40').

The feeding modules (40 and 40') thus receive the halves of the corresponding product pieces via force of gravity and a pushing element (not shown) drives the halves of the product pieces towards a sliding device (30) which guides said product pieces towards an initial toasting chamber and a second toasting chamber (not shown) of the toaster module (50). Presence sensing devices (30c) detect the passage of the bread piece halves over the sliding device, and the presence sensors (30c) thus send a corresponding detection signal to the control module and in response thereto activate the operation of the toaster module (50).

The sliding devices (30 and 30') have similar structural elements and characteristics, likewise, the feeding modules (40 and 40') have similar structural elements and characteristics. To facilitate understanding of the invention, they will thus be described in detail below.

Continuing with FIG. 2, once the product piece halves are conveyed into the toasting chambers of the toaster module (50), they are retained inside the chambers by an exit device (60) that is located below the toaster module (50), so that once the toasting time has elapsed, the control module deactivates the operation of the toaster module and sends a signal to the exit element (60) that opens the route for the halves of the product pieces towards the transport device, where they slide to their opposite end for delivery of the already toasted product.

Figure 3A:
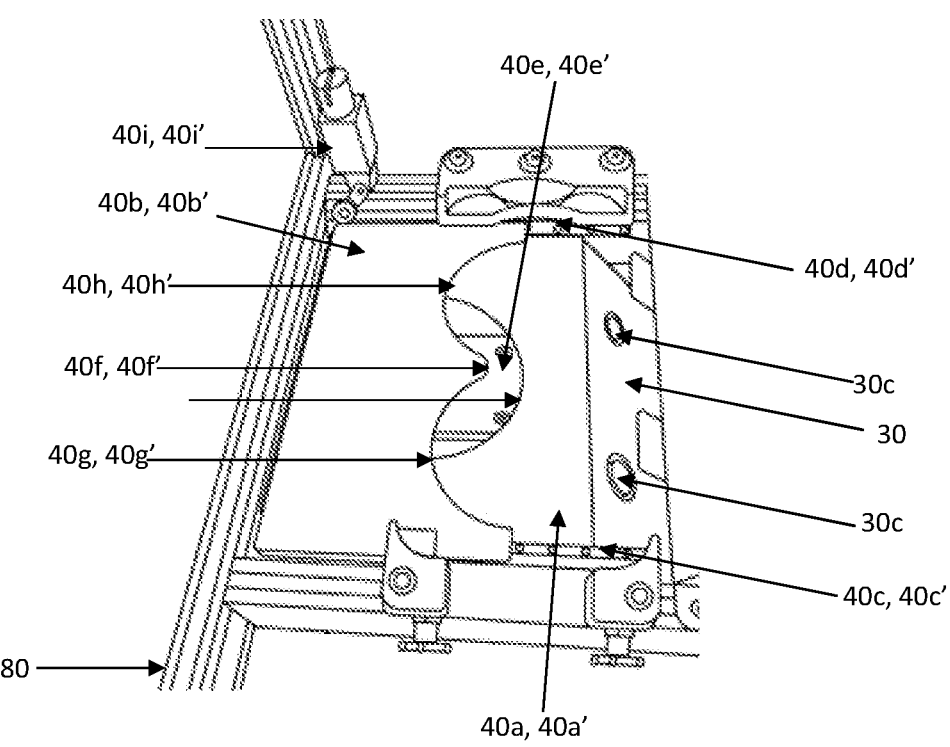
FIG. 3A shows a perspective view of one of the "standby" feed modules mounted on the structural frame of the toast piece vending machine.

Reference is made to FIG. 3A which shows a power module (40 or 40') in a "standby" state mounted on the structural frame (80) of the housing (8). Each feed module (40, 40') comprises a fixed element (40a, 40a') and a pusher element (40b, 40b') that slides horizontally as seen in FIG. 4B by means of a pair of rails (40c, 40c', 40d, 40d') and sliding devices that are arranged at a front end and a rear end respectively of the pusher element (40b, 40b').

Figure 3B:
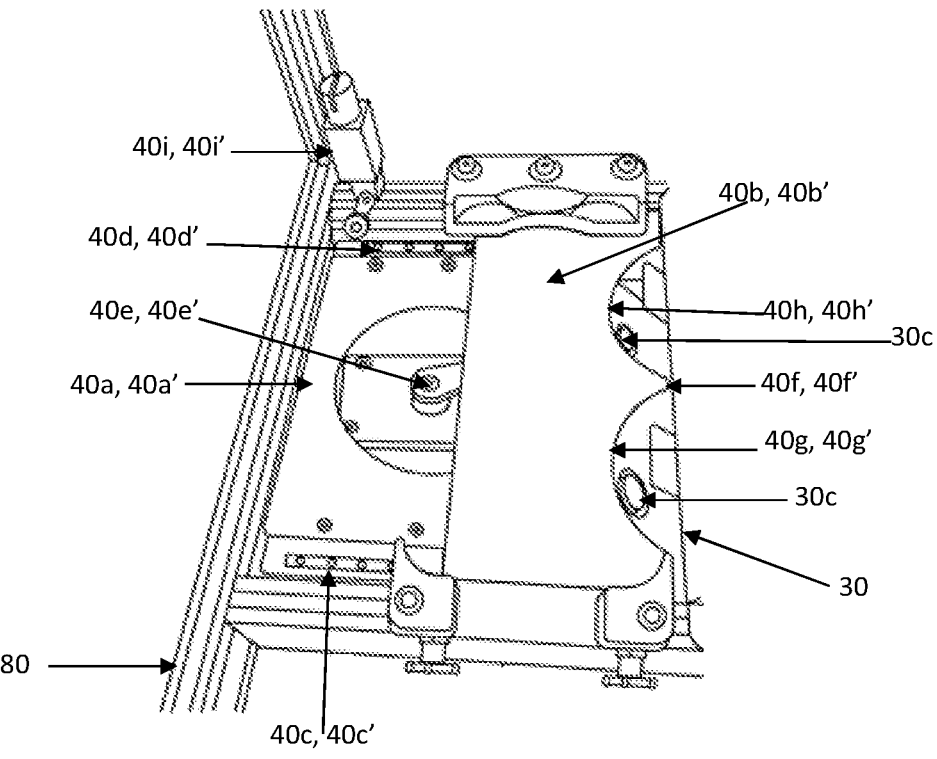
FIG. 3B shows a perspective view of one of the feed modules performing its "push" function mounted on the structural frame of the toast piece vending machine.

According to FIGS. 3A and 3B, the fixed element (40a, 40a') consists of a plate with a perforation in its centre where it passes through a connecting rod mechanism (40e, 40e') which is coupled to the lower surface of the pusher element (40b, 40b'). In this way, a motor (not shown) transmits the rotational motion towards the connecting rod mechanism causing a horizontal displacement on the thrust element (40b, 40b') and thus pushes the product piece halves towards the sliding device (30) as shown in FIG. 3b.

A position sensor (40i, 40i') detects when the thrust element (40b, 40b') returns to a "standby" state as shown in FIG. 4A. The sensor sends a signal to the control module to deactivate motor operation, whereby the power module (40 or 40') will remain in a "standby" state until the control module processes a new product purchase by a user.

According to FIGS. 3A and 3B, the pushing element (40b) comprises at its pushing side end (40f) a pair of semicircular recesses (40g and 40h) into which the halves of the product pieces are fitted so that they are pushed or directed towards the sliding devices (30). As shown in FIG. 3B.

Figure 4:
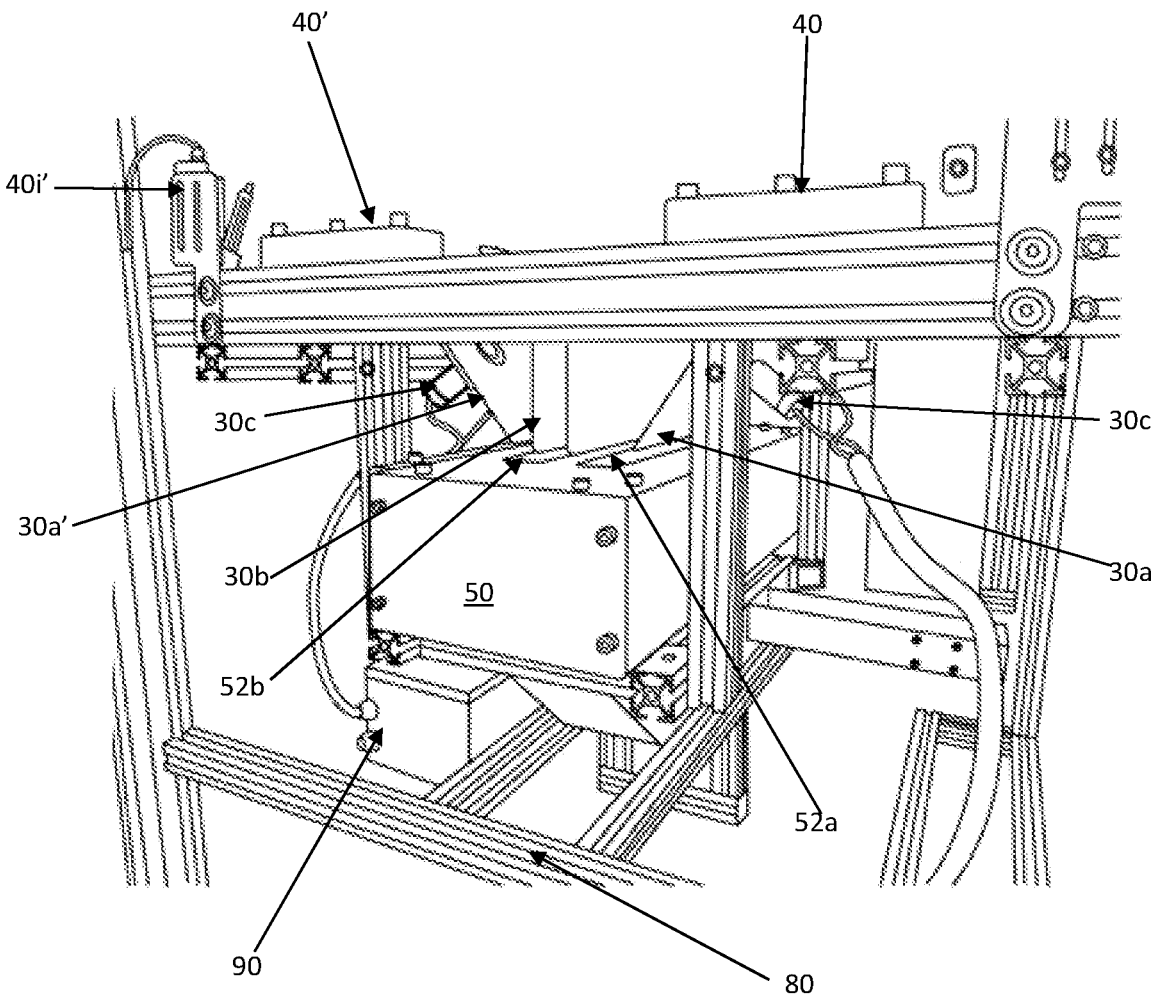
FIG. 4 shows a rear perspective view of a section of the toast piece vending machine without the storage device.

With regard to FIGS. 4 and 2, the sliding device (30) consists of a pair of inclined plates (30a and 30a') projecting at an angle below the corresponding feed module (40 and 40'); and a divider plate (30b) separating the pair of plates (30a and 30a'). In a preferred embodiment of the invention, the plates (30a or 30a') and the fixed element of the feed module (40 or 40') form a single piece.

Each plate, (30a or 30a'), in conjunction with the divider plate (30b), guides a pair of halves of a product piece into one of the toasting chambers (52a and 52b). Likewise, each of the inclined plates, (30a and 30a'), comprises a pair of perforations equidistant on its central vertical axis wherein are coupled the presence sensors (30c) wherein each presence sensor (30c) is used to detect the passage of one half of a piece of product and send the corresponding signal to the control module and send a control signal to a power control module (90) to power up the toaster module (50).

Figure 5A:
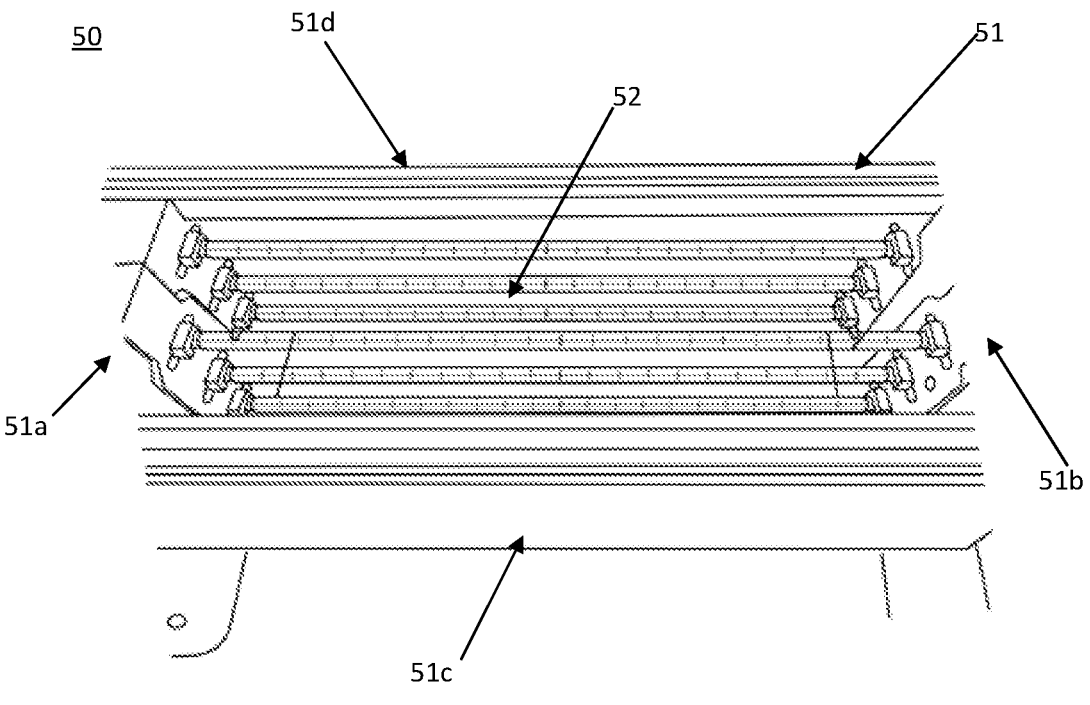
FIGS. 5A, 5B and 5C show different views of the toaster module of the toasted bread piece vending machine detailed in the present invention.

Referring to FIG. 5A, the toaster module (50) comprises an outer casing (51) with a pair of side walls, (51a and 51b), as well as also a front wall (51c) and a rear wall (51d). The outer casing (51) defines a toasting area (52) inside toasting area (52) which is divided into an initial toasting chamber (52a) and a second toasting chamber (52b), wherein each toasting chamber (52a, 52b) has an upper opening that fits into the upper openings of the housing (51) and a lower opening that fits into the lower openings of the housing (51).

The toasting area (52) is surrounded by the walls of the housing (50) and an initial arrangement of tubular heating elements (53a) close to the front wall (51c) and a second arrangement of tubular heating elements (53b) close to the rear wall (51d). A third arrangement of tubular heating elements (53c) divides the toasting area (52) into the two toasting chambers (52a and 52b). As such, the inner surfaces of the front (51c) and rear (51d) walls of the housing also serve as heat reflecting elements.

Figure 5B:
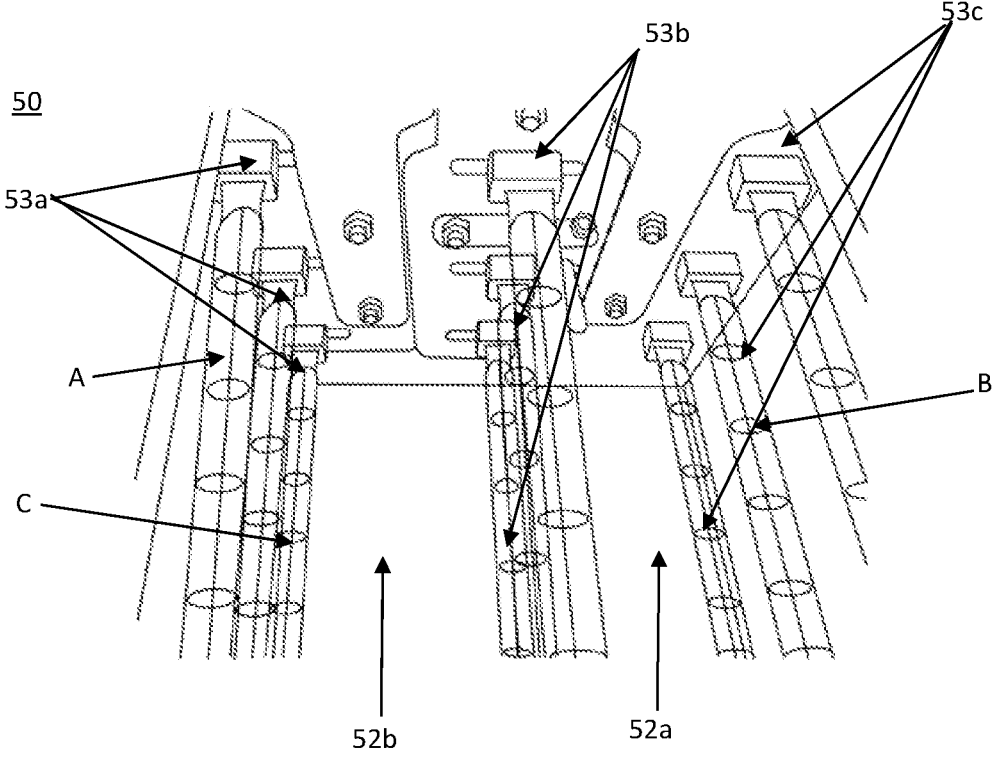

As shown in FIG. 5B, the heating elements of each array (53a, (53b and 53c) are arranged in a vertical plane and when they are powered up they radiate the heat generated by them onto the upper and lower surfaces of the product pieces to be toasted. Each heating element array comprises an upper tubular heating element (A), a middle tubular heating element (B) and a lower tubular heating element (C), spaced equidistantly and horizontally. Tubular heating elements can be quartz-halogen tubular lamps.

Figure 5C:
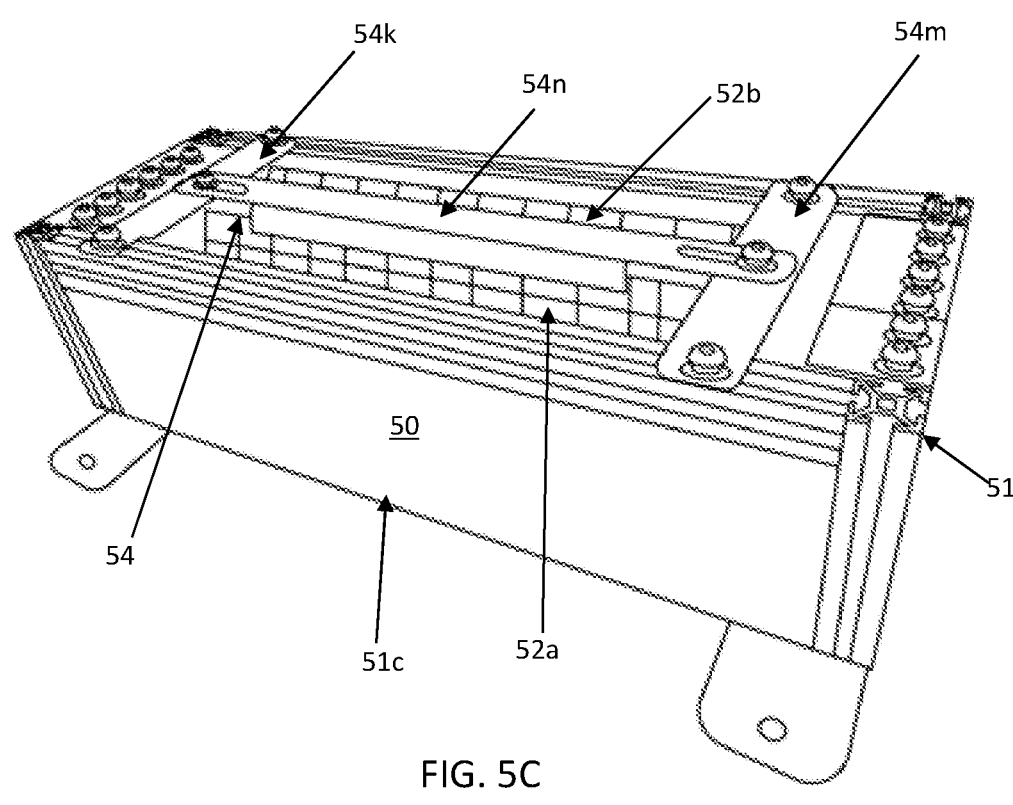

According to FIG. 5C, an open protection frame (54) is attached inside the toasting area (52) and limits the space of the two toasting chambers (52a and 52b). The open protective frame (54) thus delimits a space to ensure that the halves of the product pieces, during the toasting process, do not make direct contact with the tubular heating elements of the setup (53a,53b and 53c). In this way, the surfaces of the product parts receive more uniform heat radiation during toasting.

Figure 5D:
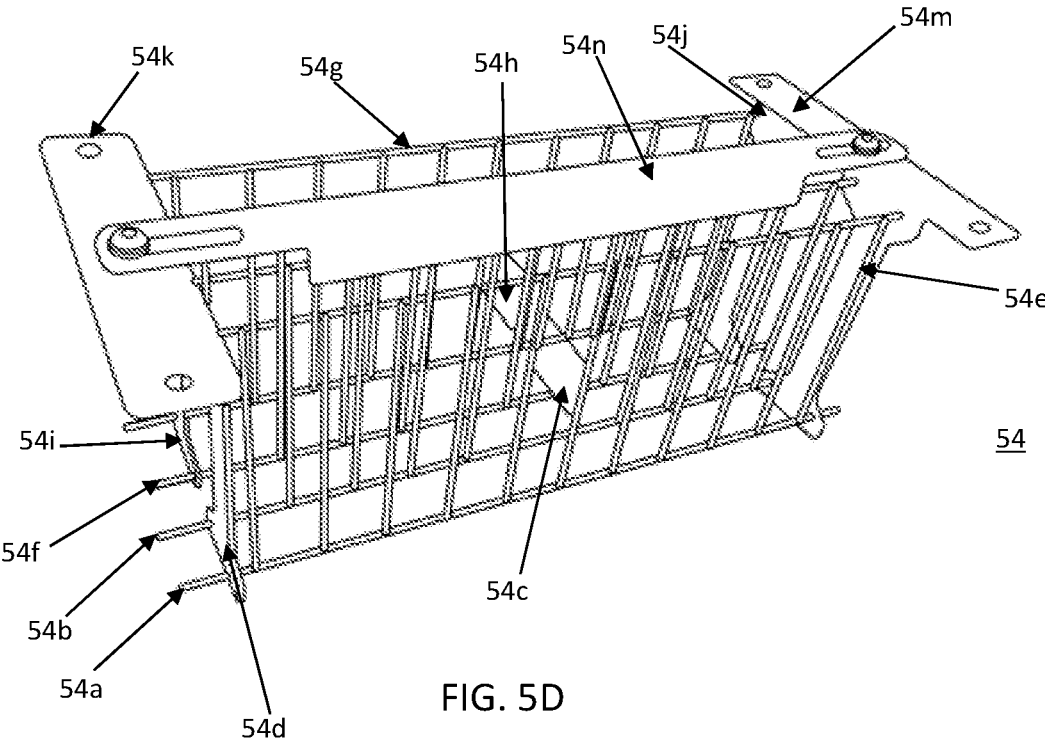
FIG. 5D shows a side perspective view of the open protective frame of the toaster module.

Particularly, FIG. 5D shows in detail the open protection frame (54) of the toaster module (50) comprising an initial grid arrangement consisting of an initial metal mesh structure (54a) and a second metal mesh structure (54b) spaced from each other in a parallel plane by a metal spacer element (54c) and joined at their lateral ends by an initial metal support (54d) and a second metal support (54e) establishing a first toasting area divided in half by a metal separating element (54c) in the first toasting chamber (52a), suitable for receiving a first pair of pieces of product to be toasted to be toasted.

Continuing with FIG. 5D, the open protective frame (54) further comprises a second grid arrangement consisting of a third metal mesh structure (54f) and a fourth metal mesh structure (54g) spaced from each other in a parallel plane by a metal spacer element (54h) and joined at their lateral ends by a third metal support (54i) and a fourth metal support (54j). The third wire mesh structure (54f) and the fourth wire mesh structure (54g) thus establish a second toasting area divided in half by a metal separating element (54n) in the second toasting chamber (52b), suitable for receiving a second pair of pieces of product to be toasted.

The initial grating arrangement and the second grating arrangement of the open protection frame (54) are joined together by a left upper plate (54k) which is welded to the upper ends of the first metal bracket (54d) and the third metal bracket (54i); and a right upper plate (54m) which is welded to the upper ends of the second metal bracket (54e) and the fourth metal bracket (54j). A transverse plate (54n) defines a space between the first grid arrangement and the second grid arrangement of the open protection frame (54), which fits and superficially covers the third arrangement of tubular heating elements of the toaster module. The cross plate (54n) is connected via its ends to the left upper plate (54k) and the right upper plate (54m) by means of fixing elements, which can include (but are not limited to) screws.

According to FIG. 5C, the open protection frame (54) is coupled inside the toasting area (52); while the upper left (54k) and upper right (54m) plates of the open protection frame (54) are fixed on the outer casing (51) of the toaster module (50) by means of fastening device which can include (but are not limited to) screws.

The toasting module (50) does not comprise a bottom wall, meaning that the toasting chambers (52a and 52b) are also open at their lower end. An outlet device (60) is located below the toaster module (50).

Figure 6A:
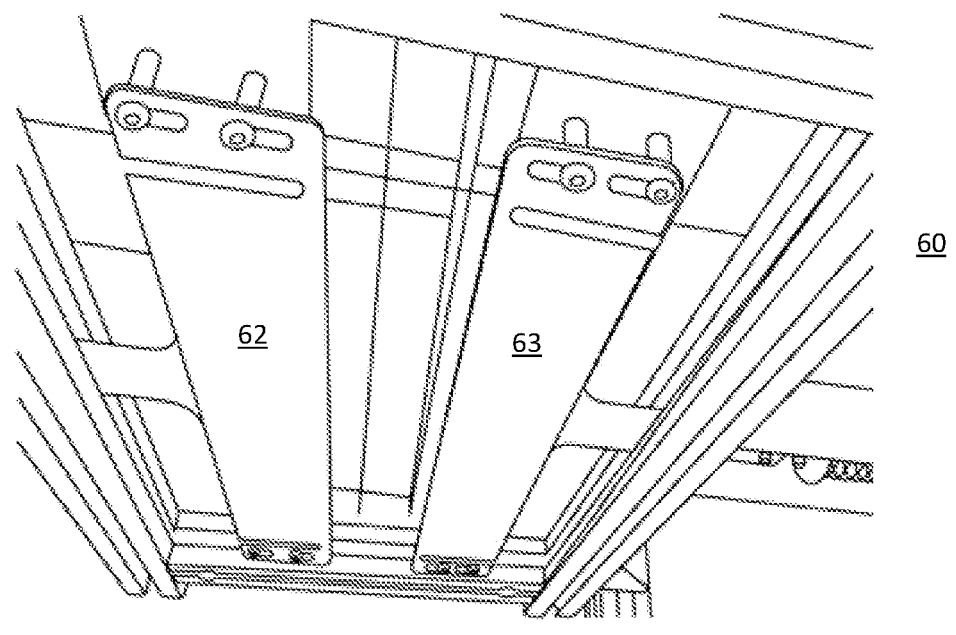
FIG. 6A shows the output module of the toast piece vending machine detailed in the present invention, in a closed state.

According to FIG. 6A, the outlet device (60) comprises a structural frame (61) with a pair of gates (62 and 63) wherein each gate is aligned at the bottom of each toasting chamber (52a, 52b). This is done in such a way that the pair of gates (62 and 63) normally remain in a "closed" state, retaining the halves of the product pieces inside the toasting chambers of the toaster module. The toasting chambers (52a and 52b) comprise a temperature sensor inside.

Figure 6B:
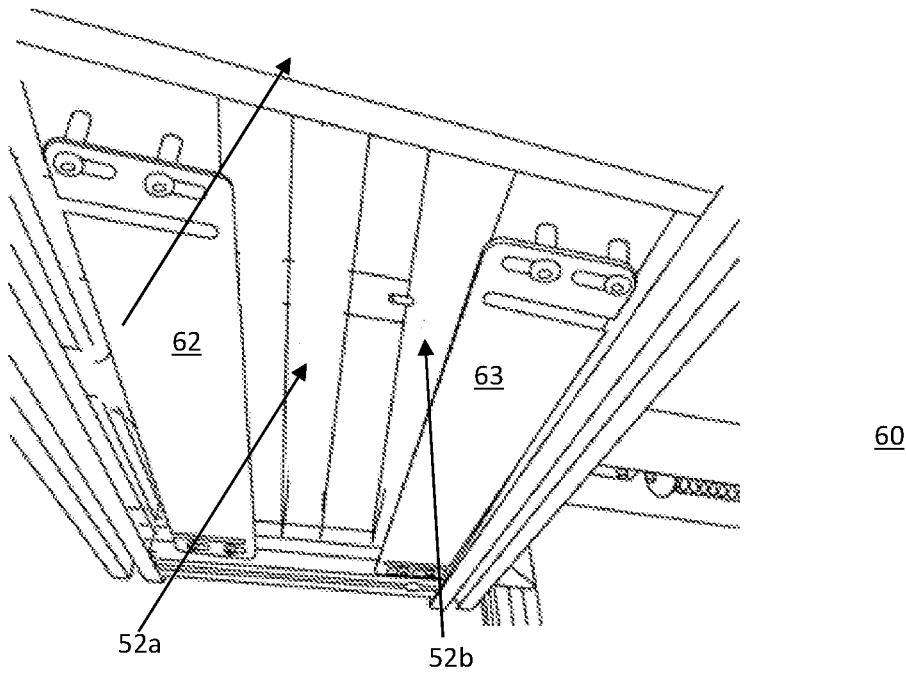
FIG. 6B shows the output module of the toast piece vending machine detailed in the present invention.

In this way, according to FIG. 6B, once, once the toasting time has elapsed, the control module sends an activation signal to the output module (60) to open its gates by sliding to its sides through spring mechanisms activated by solenoids, thus allowing the passage of the toasted bread piece halves out of the toasting chambers.

The toasted bread halves thus fall onto the transport device (70). According to FIGS. 7 and 1, the conveying device consists of a one-piece body with a corrugated surface and side walls projecting below the outlet module (60). The conveying device (70) comprises an initial conveying channel (71) receiving the halves of a pre-toasted piece of one type of bread, a second conveying channel (71) receiving the halves of a pre-toasted piece of a second type of bread and a third channel (73) separating the first conveying channel (71) from the second conveying channel (72). The corrugated surface of the conveying device (70) functions as a type of slide and the shape of said surface reduces the speed of the halves of the already toasted bread pieces as they slide towards the outlet end (74) with a stop wall (75) being used to prevent the products from being ejected out of the vending machine detailed in the present invention.

Figure 7:
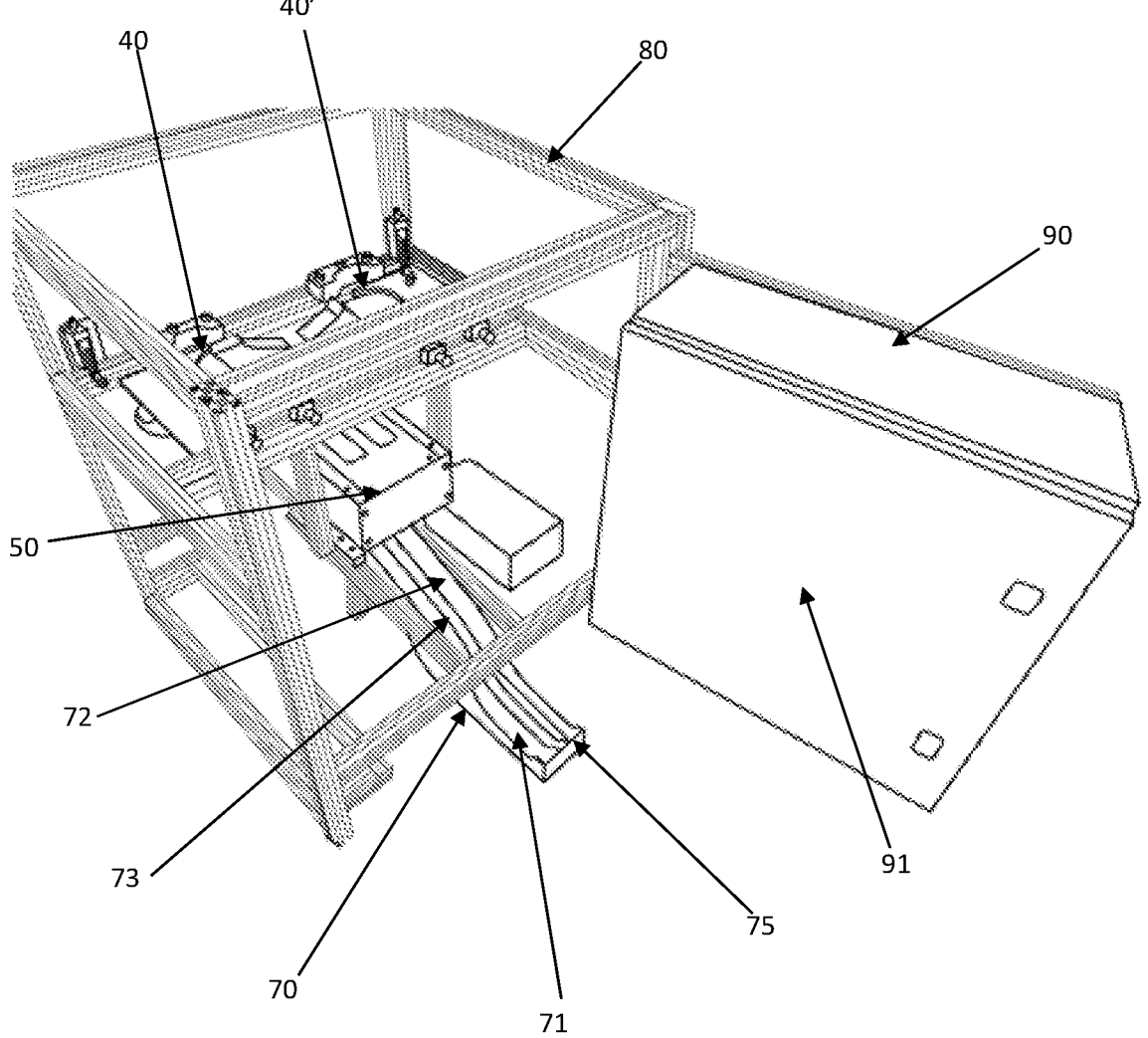
FIG. 7 shows a top side perspective of the toast piece vending machine housing without its side and rear walls, and without the product storage device.

Continuing with FIG. 7, the control module is housed within a housing (90) that is located behind the pivoting upper front wall (80d) of the housing (80) comprising a door (81) for access to the internal elements of the control module (10).

Figure 8:
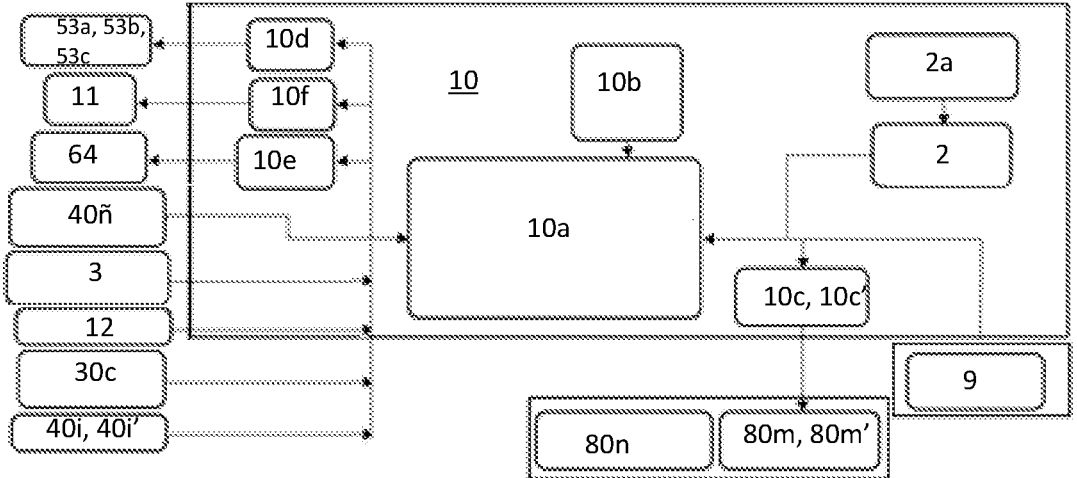
FIG. 8 shows a block diagram of the control module in connection with the electrical-electronic devices making up the toast vending machine detailed in the present invention.

FIG. 8 shows a block diagram of the elements that make up the control module (10) as well as its electrical connection with the other elements of the modules comprising the machine detailed in the present invention.

The control module (10) comprises a main power source (10b) that powers up a microcontroller or controller device (10a) in connection with the screen (not shown) that displays at least one graphical interface related to the product for sale, as well as advertising information for the user. Likewise, contactless sensors of the input interface (3) and a payment system (9) are connected to a controller device (10a) wherein the user makes at least one desired product purchase through the vending machine detailed in the present invention. A separate power supply (2a) supplies power to display 2.

The controlling device (10a) activates the operation of the pair of motors (80m, 8m') of the power supply modules (40 and 40', not shown) by means of a (80m, 8m') controller (10c) (10c') for each motor (80m, 8m') which are powered up through a second power supply source (80n), in this way the power supply modules push the halves of the piece(s) of product(s) chosen by the user or customer towards the toaster module.

The controller device (10a) comprises an electrical connection with the position sensors (40i) (40i') of the product supply modules to determine the status and operation of said modules, and based on the values registered by the sensors the controller device (10a) activates or deactivates the operation of the motors.

Continuing with FIG. 8, the presence sensors (30c) detect the passage of the product halves to be toasted into the toaster module and send a corresponding electrical signal to the controller device (10a) which uses solid-state relays (10d) to power up each arrangement of tubular heating elements (53a, 53b and 53c) of the toaster module. Furthermore, the controller device (10a) has an electrical connection with the pair of temperature sensors (40ñ) of the toasting module as a safety measure to ensure correct operation of the toasting module.

Once the toasting time previously established in the machine control logic has elapsed, the controller device (10a) powers down the tubular heating elements (53a, 53b and 53c) of the toaster module; and by means of gate relays (10e) powers up the solenoid coils (64) so that they open the gates of the output medium (60) and allow the passage of the halves of the already toasted product pieces towards the transport medium for their delivery to the user.

Additionally, the controller device (10a) uses a relay (10f) to control the operation of the UV lamp (11) to disinfect the outlet end of the transport device which is exposed to the environment outside the vending machine of the invention.

The controller device (10a) may thus include one or more inputs for receiving input data from modules or sensors. The processor controller device (10a) may be adapted to process the input data and to compare the processed or raw data with one or more stored threshold values or desired averages, or to process the input data and compare the processed or raw data with one or more desired values depending on the circumstances; it includes a controller and a memory storing the control logic.

A PIR sensor (12) detects the presence of a user in front of the machine, ensuring that the controller device control module (10a) does not activate the operation of the relay (100 and that the UV lamps (11) remain off.

The present control module, or certain parts or functions thereof, may be implemented using hardware, software, or a combination thereof, and may be implemented in one or more computer systems or other processing systems. The computer system may include a main memory, e.g., random access memory (RAM), and may also include secondary memory or in-memory (non-rotating) hard disks. The secondary memory may include, for example, a hard disk drive and/or a removable storage unit, corresponding to a disk drive, a magnetic tape drive, an optical disk drive, etc. The removable storage unit reads and/or writes to a removable storage unit in a well-known manner. The removable storage unit corresponds to a disk, magnetic tape, optical disk, solid state memory, etc., which a removable storage unit reads from or writes to. As will be seen, the removable storage unit includes a computer-usable storage medium on which computer software and/or data is stored.

In various embodiments, the secondary memory may include other similar devices to allow the control logic to be established in the computer system. Such devices may include, for example, a removable storage unit and an interface. Examples may include a programme cartridge and cartridge interface (such as found in video game devices), a removable memory chip (such as an erasable programmable read-only memory (EPROM), or a programmable read-only memory (PROM)) and an associated connector, as well as other removable storage units and interfaces, which allow instructions and data to be transferred from the removable storage unit to a computer system.

The invention claimed is:

1. A vending machine for pieces of toasted bread, characterised in that the vending machine comprises:
   a control module;
   a screen in communication with the control module that displays a graphical interface for the sale of a product;
   an input interface consisting of a plurality of non-contact sensors for user selection of a desired type and quantity of the product and positioned beyond the screen;
   a storage device where an inventory of two different types of the product for sale is stored;
   a pair of product feed modules set up below the storage device where each feed module is configured to receive a pair of pieces of selected product by force of gravity and pushes them towards a sliding device which moves the received pair of pieces of selected product towards a toaster module for toasting;
   the toaster module comprising a toasting chamber with an open product inlet and outlet, the toaster module configured to toast the received pair of pieces of selected product, resulting in toasted product pieces; and
   an exit device located below the outlet of the toaster module which is configured to pass the toasted product pieces out of and underneath the toaster module to a conveying device, whereby each of the toasted product pieces slides out of the machine through the conveying device.

2. The vending machine according to claim 1, characterised in that it further comprises a UV lamp for disinfecting an outlet end of the conveying device.

3. The vending machine according to claim 1, characterised in that the storage device comprises a plurality of containers including a left front container, a left rear container, a right front container, and a right rear container, wherein the left front container and left rear container each stores a first half and a second half, respectively, of a piece of a first type of product of the two different types of the product; and wherein the right front container and the right rear container stores a first half and a second half, respectively, of a piece of a second type of product of the two different types of the product.

4. The vending machine according to claim 3, characterised in that each of the plurality of containers of the storage device has an upper end where the product is reloaded and an open lower end configured to output the pair of pieces of selected product to the pair of product feed modules.

5. The vending machine according to claim 1, wherein the plurality of non- contact sensors is activated by a hand gesture of a user.

6. The vending machine according to claim 1, wherein the plurality of non- contact sensors recognizes a user allowing the selected product to be dispensed without physical payment by the user.

7. The vending machine according to claim 1, wherein the sliding device further comprises a pair of inclined plates, each inclined plate projecting below each feed module and divided by a divider plate.

8. The vending machine according to claim 7, wherein each inclined plate further comprises a pair of perforations equidistant to a central vertical axis, the pair of perforations adapted to receive a sensor.

9. The vending machine according to claim 1, wherein the toaster module further comprises an outer casing defining a toasting area and having a pair of side walls, a front wall, and a rear wall.

10. The vending machine according to claim 9, wherein the toasting area further comprises a plurality of front tubular heating elements proximal to the front wall, a plurality of rear tubular heating elements proximal to the rear wall, and a plurality of central tubular heating elements proximal to the center of the toasting area.

11. The vending machine according to claim 10, wherein the tubular heating elements are quartz-halogen tubular lamps.

12. The vending machine according to claim 1, characterised in that it further comprises a housing comprising a structural frame and side walls.

13. The vending machine according to claim 12, further comprising a front wall having a pivoting upper front wall attached to the structural frame and a lower front wall having dimensions smaller than the pivoting upper front wall.

14. The vending machine according to claim 13, further comprising a PIR sensor in communication with the control module and attached to a surface of the pivoting upper front wall.

15. The vending machine according to claim 14, wherein the PIR sensor detects the presence of a user in front of the vending machine and signals the control module to deactivate operation of a UV lamp mounted at a lower end of the pivoting upper front wall.

* * * * *